(12) United States Patent
Bos

(10) Patent No.: US 9,468,779 B2
(45) Date of Patent: *Oct. 18, 2016

(54) VISCOELASTIC GEL FOR DERMATOLOGICAL USE

(71) Applicant: ANTEIS SA, Plan-les-Ouates, Geneva (CH)

(72) Inventor: Gilles Bos, Plan-les-Ouates (CH)

(73) Assignee: ANTEIS SA, Geneva (CH)

(*) Notice: Subject to any disclaimer, the term of this patent is extended or adjusted under 35 U.S.C. 154(b) by 123 days.

This patent is subject to a terminal disclaimer.

(21) Appl. No.: 14/180,862

(22) Filed: Feb. 14, 2014

(65) Prior Publication Data

US 2014/0162975 A1    Jun. 12, 2014

Related U.S. Application Data

(63) Continuation of application No. 12/159,856, filed as application No. PCT/FR2007/000016 on Jan. 5, 2007, now Pat. No. 8,685,944.

(30) Foreign Application Priority Data

Jan. 6, 2006 (FR) ..................................... 06/00138

(51) Int. Cl.
| | |
|---|---|
| C08B 37/08 | (2006.01) |
| A61Q 19/00 | (2006.01) |
| A61K 8/34 | (2006.01) |
| A61K 8/73 | (2006.01) |
| A61K 9/00 | (2006.01) |
| A61K 47/10 | (2006.01) |
| A61Q 19/08 | (2006.01) |
| A61K 31/728 | (2006.01) |

(52) U.S. Cl.
CPC ............... *A61Q 19/00* (2013.01); *A61K 8/345* (2013.01); *A61K 8/735* (2013.01); *A61K 9/0019* (2013.01); *A61K 31/728* (2013.01); *A61K 47/10* (2013.01); *A61Q 19/08* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 4,303,676 A | 12/1981 | Balazs | |
| 5,106,615 A | 4/1992 | Dikstein et al. | |
| 5,604,200 A * | 2/1997 | Taylor-McCord | A61K 9/06 424/600 |
| 5,906,997 A | 5/1999 | Schwartz et al. | |
| 7,060,287 B1 | 6/2006 | Hubbard et al. | |
| 8,685,944 B2 * | 4/2014 | Bos | A61K 8/345 514/54 |
| 2003/0034264 A1 | 2/2003 | Hamai et al. | |
| 2004/0185021 A1 | 9/2004 | Hubbard | |
| 2004/0265389 A1 | 12/2004 | Yui et al. | |

FOREIGN PATENT DOCUMENTS

| | | |
|---|---|---|
| EP | 0705878 | 4/1996 |
| JP | 10306103 | 11/1998 |
| JP | 10306103 A | 11/1998 |
| JP | 2003507351 A | 2/2003 |
| WO | 0112247 A1 | 2/2001 |
| WO | 2004/073759 | 9/2004 |

OTHER PUBLICATIONS

Japanese Office Action dated Jun. 20, 2012, from corresponding JP application. (cited in parent application).
English machine translation of Japanese patent publication H10-3061 03, downloaded from JPO website Mar. 19, 2013 (cited in parent application).
Shimada et al., "Viscosity and Molecular Weight of Hyaluronic Acids" J. Biochem (1975) vol. 78 pp. 513-517 (cited in parent application).
Bouchard et al. "Properties of Sugar, Polyol, and Polysaccharide Water-Ethanol Solutions", American Chemical Society, J. Chem. Eng. Data 2007, 52, pp. 1838-1842 (copy attached).
Wik et al., "The Chemistry Biology and Medical Applications of Hyaluronan and its Derivatives" 1998 Portland Press Ltd. London, "Rheology of hyaluronan", Pharmacia & Upjohn, Book extract Hyaluronan (copy attached).
Ascher et al. "Soft Tissue Filling With Hyaluronic Acid" Annales de chirurgie plastique esthétique 49 (2004) 465-485 (copy attached).
"ASPH Guidelines on Pharmacy-Prepared Ophthalmic Products", Drug Distribution and Control: Preparation and Handling Guidelines, 1993, pp. 32-33 (copy attached).
Wikipedia "autoclave", Jan. 8, 2014 (copy attached).

* cited by examiner

*Primary Examiner* — Eric Olson
(74) *Attorney, Agent, or Firm* — Young & Thompson

(57) ABSTRACT

The invention relates to a polysaccharide gel of natural origin for dermatological use that comprises an aqueous solution of the polysaccharide of 0.1 to 5% by weight/volume, for example hyaluronic acid, and a viscous and strongly hydrophilic biocompatible alcohol at 0.5-5% by weight/volume, for example glycerol, and optionally the adjuvants that are commonly used in dermatology. The gel is prepared by mixing the polysaccharide solution and the strongly hydrophilic viscous alcohol before sterilizing the entire mixture by, for example, moist heat.

6 Claims, 3 Drawing Sheets

VISCOELASTIC GEL FOR DERMATOLOGICAL USE

Figure 1:
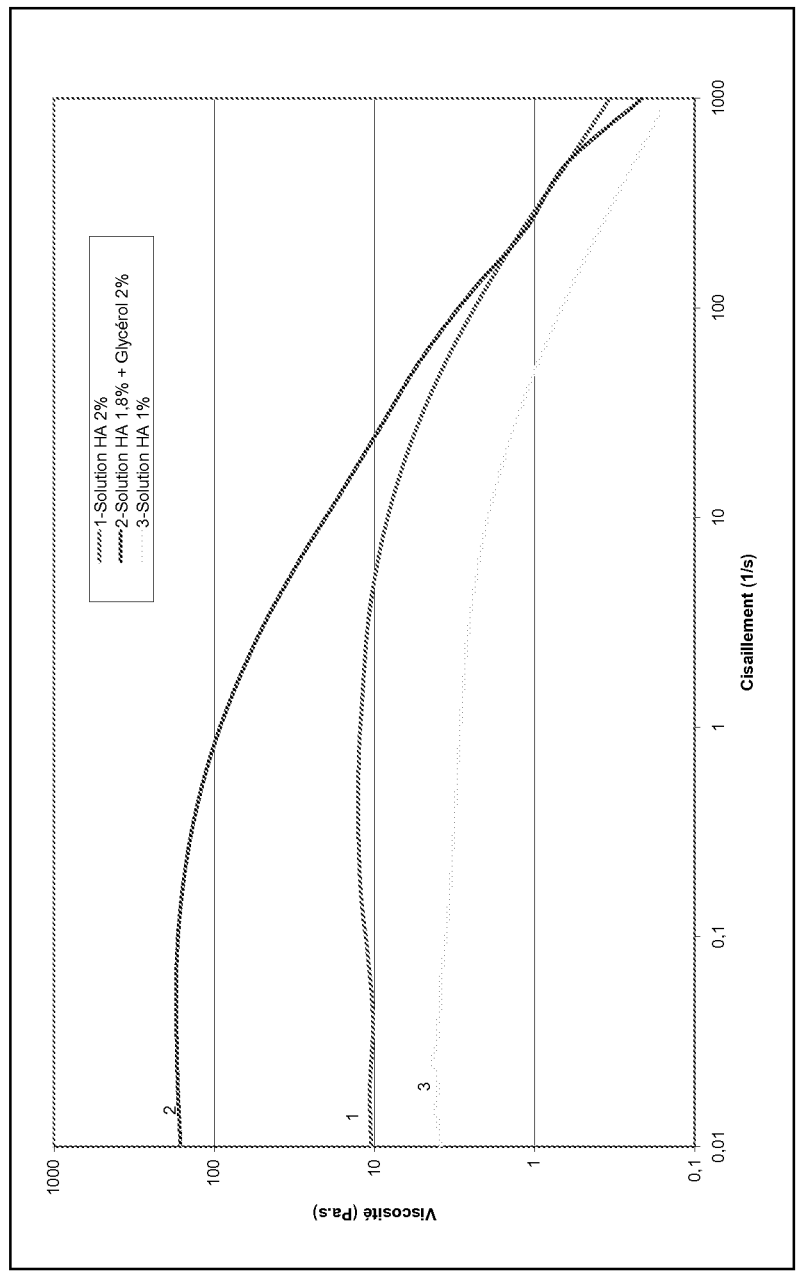

The invention relates to a viscoelastic gel for dermatological use.

Various polymers of natural origin such as collagen, hyaluronic acid or cellulosic derivatives are frequently used in aesthetic medicine and in dermatology for filling in wrinkles, remodeling the face, increasing the volume of the lips, and rejuvenating the skin of the face; this last type of treatment is derived directly from mesotherapy.

For rejuvenating the skin, the practitioners frequently use hyaluronic acid, sometimes combined with complexes of vitamins, amino acids, mineral salts and nucleic acids.

The object of this invention consists of the combination of a polysaccharide of natural origin, more particularly hyaluronan, and a viscous alcohol so as to propose an injectable ready-to-use composition that optimizes the rejuvenation treatment of the skin, in particular that involves a polysaccharide gel of natural origin that is used as an injection in dermatology, comprising an aqueous polysaccharide solution at 0.1-5% by weight/volume and a viscous and strongly hydrophilic biocompatible alcohol at 0.5-5% by weight/volume, obtained by preparation of an aqueous solution of the polysaccharide and alcohol, then sterilization of this solution, and optionally the adjuvants that are commonly used in dermatology, sterilization after mixing the components having the effect of considerably increasing the viscosity of the resulting gel.

It has actually been found that the combination of a polysaccharide or its salts, in particular hyaluronan or sodium hyaluronate, and a small amount of a biocompatible viscous alcohol provides a composition whose viscosity greatly increases, and that when the biocompatible viscous alcohol is also hydrophilic, it considerably increases the water retention properties when the composition is injected under the skin that is to be treated.

Hydrophilic compound is defined as any compound that has a strong affinity for water. In an alcohol, the higher the density of OH groups, the more hydrophilic it is. For example, the glycerol, alcohol of low molecular weight (92.09 g·mol) and containing three OH groups, is extremely hydrophilic.

It has been found that the addition of a small amount, on the order of 0.5 to 5% by weight/volume, of a biocompatible viscous alcohol brings about a significant increase of the viscosity of a polysaccharide solution of natural origin at 0.1-5% by weight/volume, stabilizes this solution during the sterilization, and maintains particularly advantageous viscous properties for the rejuvenation of cutaneous tissue. The viscous alcohol can participate in the restructuring of the skin and the maturation of cells of this tissue and ensures the isotonicity of the mixture.

A biocompatible alcohol that has antiseptic properties, which reduces this risk of cutaneous infections, is preferably used. Actually, this risk is significant during a rejuvenation treatment, taking into account the large number of injections made in the face. Examples of such alcohols are in particular glycerol and polyethylene glycol lauryl sulfate.

Commercial hyaluronic acids have different molecular weights (MW) and different concentrations according to the manufacturer. By way of illustration, it is possible to use a concentration of 1.8% by weight/volume for hyaluronic acid of low to medium weight (0.5 to 1.8 MDa) and a concentration of 1.5% by weight/volume for hyaluronic acid of high weight (2.0 to 3.0 MDa).

The invention also provides a process for preparation of a polysaccharide gel of natural origin for dermatological use, comprising the stages consisting in:
a) Preparing an aqueous solution of polysaccharide and viscous and strongly hydrophilic biocompatible alcohol in the desired proportions,
b) Sterilizing the resulting solution, in particular by moist heat, and
c) Optionally putting the gel into a ready-to-use form.

Figure 2:
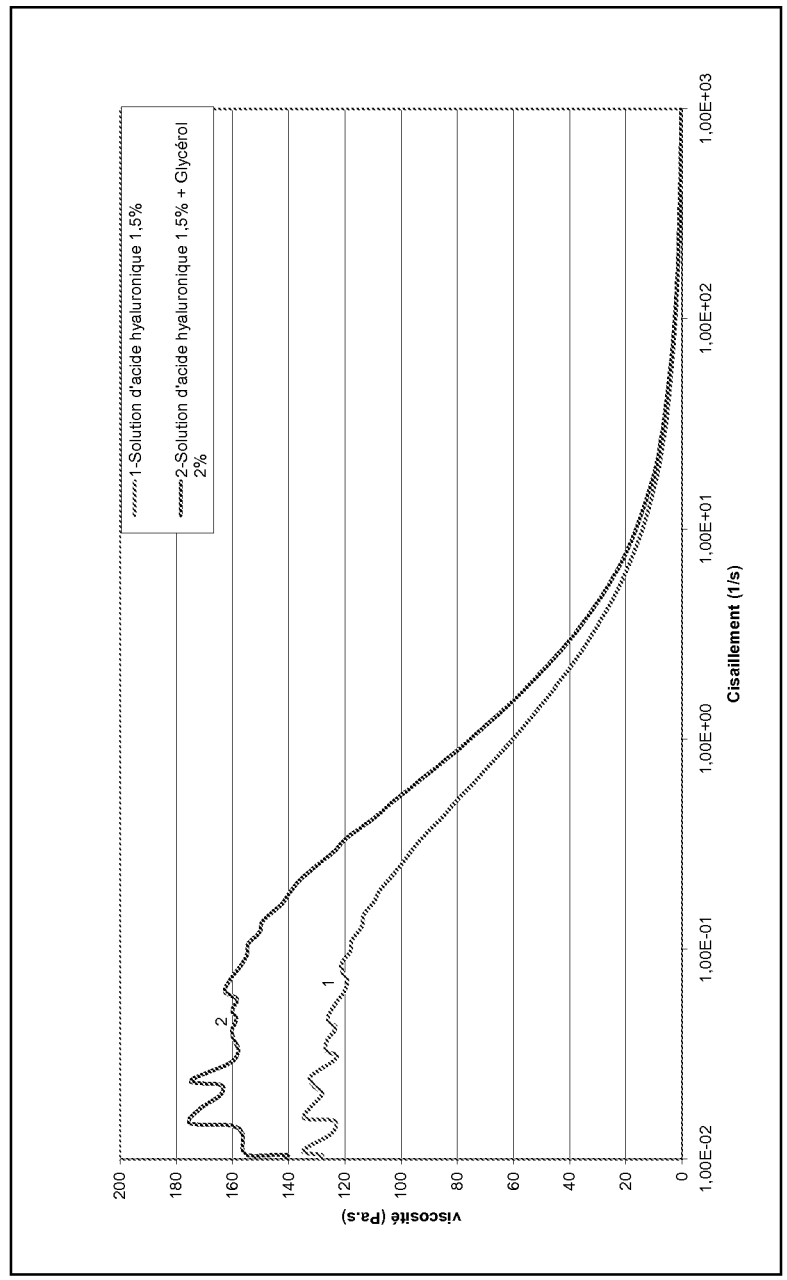
Figure 3:
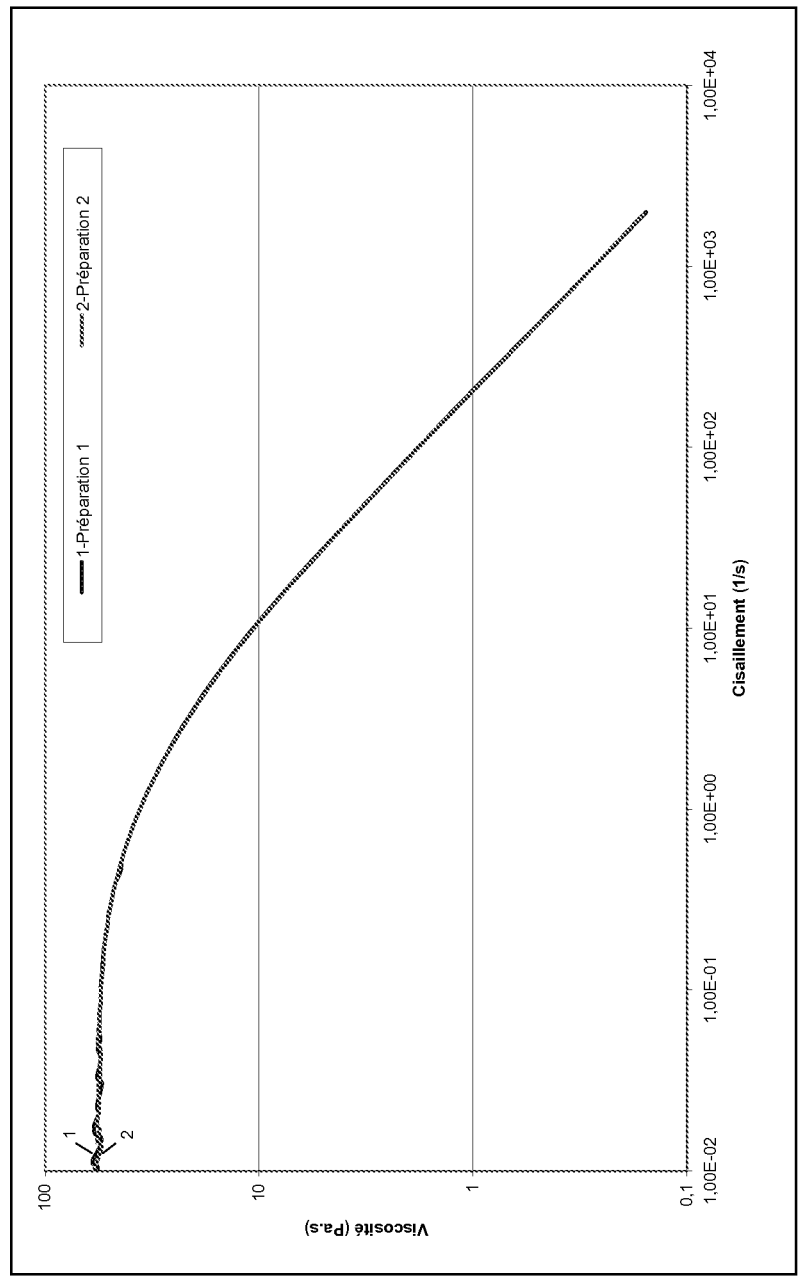

FIGS. 1 to 3 are graphs that show the viscosities of the compositions of Examples 1 and 2 according to the invention and Example 3 (for comparison).

EXAMPLE 1

Influence of the Hyaluronic Acid Concentration and the Presence of Glycerol on the Viscosity of Solutions for the Rejuvenation of the Face Three solutions based on the same hyaluronic acid that is characterized by a mean molecular weight of 1.6 MDa were prepared.

The first solution is a hyaluronic acid solution at 1%.

The second solution is a solution of the same hyaluronic acid, but concentrated at 2%.

The third solution contains only 1.8% of this same hyaluronic acid to which glycerol was added at 2% by weight/volume.

The three preparations were sterilized by moist heat, then their rheological properties were analyzed using a rheometer by measuring the viscosity based on the shear rate imposed on the product.

It clearly appears that, according to the graph of FIG. 1, for the low shear rates (corresponding to those to which the preparation is exposed for the rejuvenation of cutaneous tissue after injection), the addition of glycerol to a hyaluronic acid solution has more influence for obtaining a high-viscosity preparation than the increase of the hyaluronic acid concentration.

EXAMPLE 2

Influence of Glycerol on the Viscosity of Hyaluronic Acid Solutions with High Molecular Weight Two solutions based on hyaluronic acid, characterized by a very high mean molecular weight (2.6 MDa), were prepared.

The first preparation is a hyaluronic acid solution at 1.5%.

The second preparation also contains 1.5% hyaluronic acid with high molecular weight to which was added glycerol at 2% by weight/volume.

The two preparations were sterilized by moist heat, then their rheological properties were analyzed using a rheometer by measuring the viscosity based on the shear rate imposed on the product.

The graph of FIG. 2 demonstrates that, even when the preparation consists of a hyaluronic acid of high molecular weight—therefore initially characterized by a high viscosity—the glycerol all the same tends to increase the viscous properties of the product.

EXAMPLE 3

Stabilization of the Preparation by Glycerol During the Sterilization (for Comparison)

A solution with 1.5% hyaluronic acid, characterized by a very high mean molecular weight (2.6 MDa), was prepared. This solution was then sterilized by moist heat (preparation 1).

Glycerol was added to several milliliters of this sterilized solution (preparation 2).

No rheological difference is observed between these two preparations; the graph of FIG. 3 and the examples presented above demonstrate the stabilizing effect of glycerol during sterilization.

It is therefore essential that the viscous alcohol be mixed with the hyaluronic acid solution before the sterilization to obtain the increase in viscosity.

After sterilization, the composition can be put into a ready-to-use form, for example in an ampoule or a flask that contains the dose to be injected by means of a syringe.

The composition can comprise adjuvants that are commonly used in dermatology, added to the mixture before sterilization. Such adjuvants are vitamins, mineral acids, mineral salts, and nucleic acids.

The invention claimed is:

1. A polysaccharide gel of natural origin that is used for injection in dermatology, comprising an aqueous solution containing 1.5-5% by weight/volume of hyaluronic acid and 0.5-5% by weight/volume of a viscous and strongly hydrophilic biocompatible alcohol, obtained by preparation of an aqueous solution of the hyaluronic acid and the alcohol, then sterilization of this solution by moist heat, and optionally adjuvants that are commonly used in dermatology.

2. The gel according to claim 1, wherein the biocompatible alcohol is glycerol.

3. The gel according to claim 1, wherein the aqueous solution contains 1.8% by weight/volume of hyaluronic acid of mean molecular weight (MW) of 0.5 to 1.8 MDa and 2% by weight/volume of glycerol.

4. The gel according to claim 1, wherein the aqueous solution contains 1.5% by weight/volume of hyaluronic acid of high molecular weight (MW) of 2.0 to 3.0 MDa and 2% by weight/volume of glycerol.

5. A process for preparation of a polysaccharide gel of natural origin for dermatological use according to claim 1, comprising the steps of:
   a) preparing an aqueous solution containing 1.5%-5% by weight/volume of hyaluronic acid and 0.5%-5% by weight/volume of a viscous and strongly hydrophilic biocompatible alcohol;
   b) sterilizing the resulting solution by moist heat; and
   c) optionally putting the gel into a ready-to-use form.

6. The process according to claim 5, wherein the biocompatible alcohol is glycerol.

* * * * *